US012601726B2

(12) United States Patent
Liang et al.

(10) Patent No.: US 12,601,726 B2
(45) Date of Patent: Apr. 14, 2026

(54) METHANE MONITORING APPARATUS AND SYSTEM FOR STEREOSCOPIC AND REAL-TIME METHANE MONITORING OF OCEAN PROFILE

(71) Applicants: GUANGZHOU MARINE GEOLOGICAL SURVEY, Guangzhou (CN); Qingdao Saintblue Technology Co., Ltd., Qingdao (CN)

(72) Inventors: Qianyong Liang, Guangzhou (CN); XuWen Qin, Guangzhou (CN); Binbin Guo, Guangzhou (CN); Li Li, Qingdao (CN); Danyi Su, Guangzhou (CN); Huice He, Guangzhou (CN); Yifei Dong, Guangzhou (CN); Xuemin Wu, Guangzhou (CN); Zhigang Wang, Guangzhou (CN); Xiaoyu Wu, Guangzhou (CN)

(73) Assignees: GUANGZHOU MARINE GEOLOGICAL SURVEY, Guangzhou (CN); Qingdao Saintblue Technology Co., Ltd., Qingdao (CN)

( * ) Notice: Subject to any disclaimer, the term of this patent is extended or adjusted under 35 U.S.C. 154(b) by 409 days.

(21) Appl. No.: 18/073,616

(22) Filed: Dec. 2, 2022

(65) Prior Publication Data

US 2023/0098916 A1 Mar. 30, 2023

(51) Int. Cl.
*G01N 33/18* (2006.01)
*G01N 1/22* (2006.01)

(52) U.S. Cl.
CPC ....... *G01N 33/1886* (2013.01); *G01N 1/2247* (2013.01); *G01N 33/182* (2013.01)

(58) Field of Classification Search
CPC . G01N 1/2247; G01N 33/182; G01N 33/1886
See application file for complete search history.

(56) References Cited

U.S. PATENT DOCUMENTS

| | | | | |
|---|---|---|---|---|
| 5,208,785 A | * | 5/1993 | Brumley | G01S 15/582 |
| | | | | 367/90 |
| 2020/0339234 A1 | * | 10/2020 | Kurata | C09D 183/04 |
| 2021/0101661 A1 | * | 4/2021 | Peterson | B63B 22/003 |

FOREIGN PATENT DOCUMENTS

| | | | | |
|---|---|---|---|---|
| CN | 102167136 A | * | 8/2011 | |
| CN | 103267518 A | * | 8/2013 | |

(Continued)

*Primary Examiner* — Jill E Culler

(74) *Attorney, Agent, or Firm* — Bayramoglu Law Offices LLC

(57) ABSTRACT

A system for stereoscopic and real-time monitoring of an ocean methane profile includes a waterborne communication floating body, a gravity anchor, and a monitoring mechanism disposed therebetween, wherein the monitoring mechanism includes a submarine methane leakage intensity monitoring apparatus, a plurality of methane monitoring apparatus capable of synchronously monitoring methane content and a hydrodynamic environment, and a plastic-coated steel cable connected between the waterborne communication floating body and the gravity anchor; a data acquisition cabin is connected to the plastic-coated steel cable through a first communication module; and a first floating ball assembly is connected to the plastic-coated steel cable through a fixing rope. The submarine methane leakage intensity monitoring apparatus and the plurality of methane monitoring apparatus are disposed between the gravity anchor and the waterborne communication floating body at predetermined intervals.

12 Claims, 3 Drawing Sheets

(56) References Cited

FOREIGN PATENT DOCUMENTS

| | | | | | |
|---|---|---|---|---|---|
| CN | 106768076 | A | * | 5/2017 | ............ G01D 21/02 |
| CN | 107678055 | A | | 2/2018 | |
| CN | 109737926 | A | * | 5/2019 | |
| CN | 109835438 | A | * | 6/2019 | |

* cited by examiner

METHANE MONITORING APPARATUS AND SYSTEM FOR STEREOSCOPIC AND REAL-TIME METHANE MONITORING OF OCEAN PROFILE

TECHNICAL FIELD

The present invention relates to the field of marine environment monitoring technologies, and in particular to a methane monitoring apparatus and a system for stereoscopic and real-time monitoring of an ocean methane profile.

BACKGROUND

A submarine natural gas hydrates, which is mainly located on the continental shelf and continental slope, is a huge methane repository. It is an important source area of atmospheric methane and contributes greatly to the atmospheric methane. However, exploitation of natural gas hydrates by human beings may intensify methane leakage, and increase a risk that methane enters the atmosphere, thereby leading to catastrophic consequences such as ocean hypoxia and global warming. Therefore, it is particularly important to carry out stereoscopic and real-time monitoring of an ocean methane profile during marine carbon cycle research and marine gas hydrate exploitation.

Chinese patent CN107678055A discloses a system and method for monitoring seabed methane from marine gas hydrates. In this document, a first monitoring circle and a second monitoring circle are disposed by taking a location of an exploitation well as a center, and each of the first monitoring circle and the second monitoring circle is provided with a plurality of groups of seabed lander used for monitoring a seabed methane concentration and acquiring a seabed methane data matrix. The technical solution disclosed in this patent can only detect whether methane leakage occurs on the seabed, but cannot stereoscopically track leaked methane, and thus cannot know a destination of methane leaving the seabed and cannot accurately assess an environmental impact of methane leakage.

A process in which methane enters seawater and diffuses and migrates to the atmosphere interface involves complex actions such as dissolution, phase transition, and ocean current transport, being closely related to hydrodynamic environments such as seawater temperature, pressure, and an ocean current. Therefore, in an exploitation process of marine gas hydrates, it is necessary to synchronously monitor methane concentrations and hydrodynamic environments of a plurality of water layers and transmit data back in real time, to punctually control a diffusion and migration path and an environmental impact of methane leaking from the seabed. A previous real-time subsurface buoy that is based on an inductive coupling transmission technology can provide real-time data return, but cannot support synchronous monitoring and real-time return of ocean methane and a hydrodynamic environment.

Therefore, the present invention provides a methane monitoring apparatus and a system for stereoscopic and real-time monitoring of an ocean methane profile, to implement stereoscopic and real-time tracking of methane leaking from a seabed in a diffusion and migration process in seawater. Therefore, a necessary monitoring means is provided for environmental impact assessment of marine gas hydrate exploitation and marine carbon cycle research.

SUMMARY

In order to overcome the deficiencies of the prior art, the first objective of the present invention is to provide a methane monitoring apparatus, which can solve the problems that the existing inductive coupling transmission subsurface buoy technology cannot synchronously monitor ocean methane and a hydrodynamic environment, and punctually transmit monitored data.

The second objective of the present invention is to provide a system for stereoscopic and real-time monitoring of an ocean methane profile, which can solve the problem that the prior art cannot monitor a diffusion and migration process of methane leaking from a seabed in seawater in real time.

To achieve the first objective above, the present invention adopts the following technical solutions.

A methane monitoring apparatus includes: a plurality of first floating ball assemblies for submerging, a real-time monitoring module for synchronous monitoring of methane content and a hydrodynamic environment in a water body, a data acquisition cabin for processing monitored data, a first communication module connected with an external communication apparatus, and a fixing rope for connecting the first floating ball assemblies and the data acquisition cabin, wherein the real-time monitoring module is connected with the first communication module through the data acquisition cabin, and the first floating ball assemblies are connected to the data acquisition cabin through the fixing rope.

Preferably, the first floating ball assemblies are sequentially arranged on the fixing rope in a monitoring direction.

Preferably, the fixing rope is a Kevlar rope.

Preferably, the real-time monitoring module includes an ocean current meter, a Conductivity Temperature Depth (CTD), and a methane sensor, and the ocean current meter, the CTD and the methane sensor are all connected to the data acquisition cabin.

Preferably, the first communication module includes an inductive coupling transmitter for communicating with the outside, and the data acquisition cabin is connected to the external communication apparatus through the inductive coupling transmitter.

Preferably, the first floating ball assembly includes a glass floating ball and a protective shell wrapping the glass floating ball, and the glass floating ball is connected to the fixing rope through the protective shell.

To achieve the second objective above, the present invention adopts the following technical solutions.

A system for stereoscopic and real-time monitoring of an ocean methane profile includes: a waterborne communication floating body, a submarine gravity anchor, and a monitoring mechanism disposed between the waterborne communication floating body and the submarine gravity anchor, wherein the monitoring mechanism includes a submarine methane leakage intensity monitoring apparatus, a plurality of methane monitoring apparatus described above, and a plastic-coated steel cable connected between the waterborne communication floating body and the gravity anchor; the submarine methane leakage intensity monitoring apparatus includes a second communication module and an acoustic Doppler current profiler (ADCP) that is disposed between the gravity anchor and the methane monitoring apparatus; the ADCP is connected to the plastic-coated steel cable through the second communication module; the data acquisition cabin of the methane monitoring apparatus is connected with the plastic-coated steel cable through the first communication module; the first floating ball assembly of the methane monitoring apparatus is connected to the plastic-coated steel cable through the fixing rope; and the plastic-coated steel cable is configured to communicate between the methane monitoring apparatus and the waterborne communication floating body.

Preferably, the system further includes an upper connector and a lower connector, wherein one end of the fixing rope is connected to a side, close to the waterborne communication floating body, of the plastic-coated steel cable through the upper connector; the other end of the fixing rope is connected to a side, close to the gravity anchor, of the plastic-coated steel cable through the lower connector; and the data acquisition cabin and the first floating ball assemblies are sequentially arranged on the fixing rope in the monitoring direction.

Preferably, the system further includes an acoustic release, wherein the plastic-coated steel cable is connected to the gravity anchor through the acoustic release; and the ADCP is disposed between the acoustic release and the methane monitoring apparatus.

Preferably, the system further includes a plurality of second floating ball assemblies, wherein a side, away from the gravity anchor, of the acoustic release is connected to the second floating ball assemblies through the fixing rope.

Compared with the prior art, the present invention has the following beneficial effects. The submarine methane leakage intensity monitoring apparatus and the plurality of methane monitoring apparatus capable of synchronously monitoring methane content and a hydrodynamic environment are disposed between the waterborne communication floating body and the gravity anchor at predetermined intervals, to synchronously monitor a methane concentration and a hydrodynamic environment of a target sea area by water layers, and stereoscopically track a diffusion and migration path, in a water body, of methane leaking from a seabed. Specifically, the submarine methane leakage intensity monitoring apparatus uses the ADCP to monitor an echo intensity of the water body and an eruption speed of submarine methane, thereby determining a leakage intensity of the submarine methane. The methane monitoring apparatus acquires and monitors methane concentrations and hydrodynamic environments of a plurality of water layers in real time, thereby determining a water layer to which methane arrives after leaving the seabed and a diffusion and migration path of the methane in a horizontal direction. The first communication module transmits monitored data to the waterborne communication floating body through the plastic-coated steel cable; and then the waterborne communication floating body punctually transmits the data to the outside. The first floating ball assembly is connected to the plastic-coated steel cable through the fixing rope, so that the fixing rope replaces the plastic-coated steel cable in bearing stress, thereby reducing a breakage risk of the plastic-coated steel cable. In addition, the first floating ball assembly provides buoyancy for the system for stereoscopic and real-time monitoring of the ocean methane profile by segments, thereby ensuring current resistance and implementing a long-term effective monitoring operation.

Figure 1:
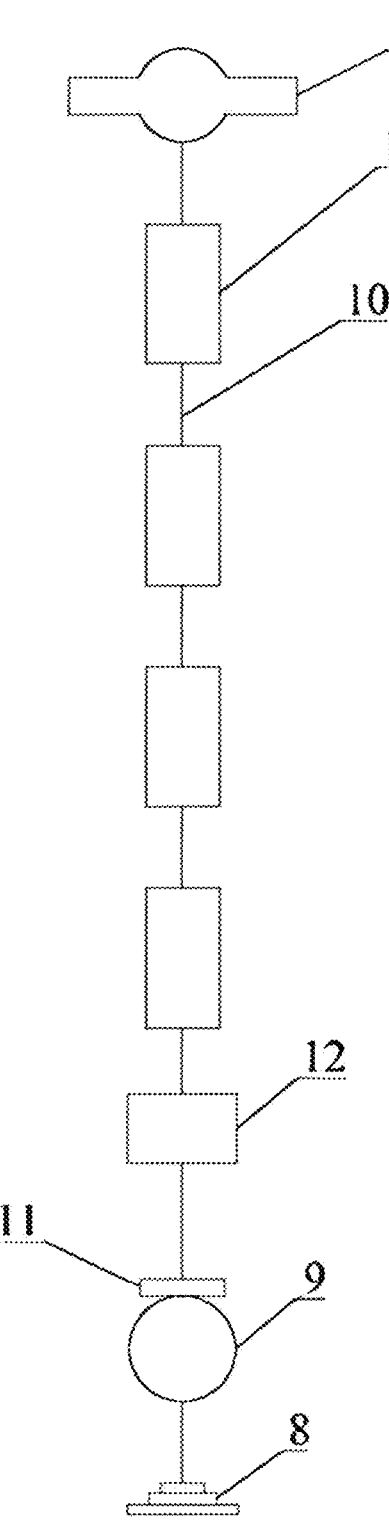
FIG. 1 is a schematic structural diagram of a system for stereoscopic and real-time monitoring of an ocean methane profile according to the present invention.

In the drawings, the list of parts represented by reference numerals is as follows: 1: methane monitoring apparatus; 2: first floating ball assembly; 3: real-time monitoring module; 31: ocean current meter; 32: CTD; 33: methane sensor; 4: data acquisition cabin; 5: first communication module; 6: fixing rope; 7: waterborne communication floating body; 8: gravity anchor; 9: acoustic release; 10: plastic-coated steel cable; 11: second floating ball assembly; and 12: submarine methane leakage intensity monitoring apparatus.

DETAILED DESCRIPTION OF THE EMBODIMENTS

Preferred embodiments of the present invention will be described below with reference to the accompanying drawings. It should be understood that the preferred embodiments described here are only used to illustrate and explain the present invention, and are not used to limit the present invention.

In the description of the present invention, it should be noted that the orientation or positional relationships indicated by the terms "center", "upper", "lower", "left", "right", "vertical", "horizontal", "inner", "outer", and the like are based on the orientation or positional relationships shown in the accompanying drawings, and are only for the convenience of describing the present invention and simplifying the description, rather than indicating or implying that the pointed apparatus or element must have a specific orientation or must be constructed or operated with a specific orientation. The orientation or positional relationships cannot therefore be understood as a limitation of the present invention. In addition, the terms "first", "second", and "third" are only used for descriptive purposes, and cannot be understood as indicating or implying relative importance.

In the description of the present invention, it should be noted that unless otherwise expressly specified and defined, terms such as "installed", "coupled" and "connected" should be comprehended in a broad sense. For example, a connection may be a fixed connection, a detachable connection, or an integral connection; and may be a mechanical connection or an electrical connection; and may be a direct connection, an indirect connection by means of an intermediary, or internal communication between two elements. For a person of ordinary skill in the art, specific meanings of the above terms in the present invention may be understood based on specific situations.

The following further describes the present invention with reference to the accompanying drawings and specific embodiments.

In the present invention, a monitoring direction is a direction from a waterborne communication floating body 7 to a gravity anchor 8. An interior of each of a first floating ball assembly 2 and a second floating ball assembly 11 is a glass floating ball having a sealed structure and then an outer surface of the glass floating ball is wrapped by a protective shell capable of submerging in water for a long time. The glass floating ball is connected to a fixing rope 6 (a Kevlar rope) through the protective shell. The Kevlar rope is woven from Kevlar® fibers. The Kevlar® fibers have an extremely high strength of greater than 28 g/denier which is 5 to 6 times that of high-quality steel, a modulus which is 2 to 3 times that of steel or glass fiber, a toughness which is twice that of steel, but a weight which is only ⅕ that of steel. In this embodiment, a plurality of first floating ball assemblies 2 or second floating ball assemblies 11 are connected in series through the Kevlar rope to provide enough buoyancy for the system, so that a real-time monitoring module 3 can be prevented from excessive vertical displacement and then monitor effectively a preset monitored water layer for a long time. The plastic-coated steel cable 10 is formed by plastic-coating an outer layer of a steel cable, and has better shock-absorbing, compression-resistant and corrosion-resistant properties than a traditional steel cable.

Embodiment I

Figure 2:
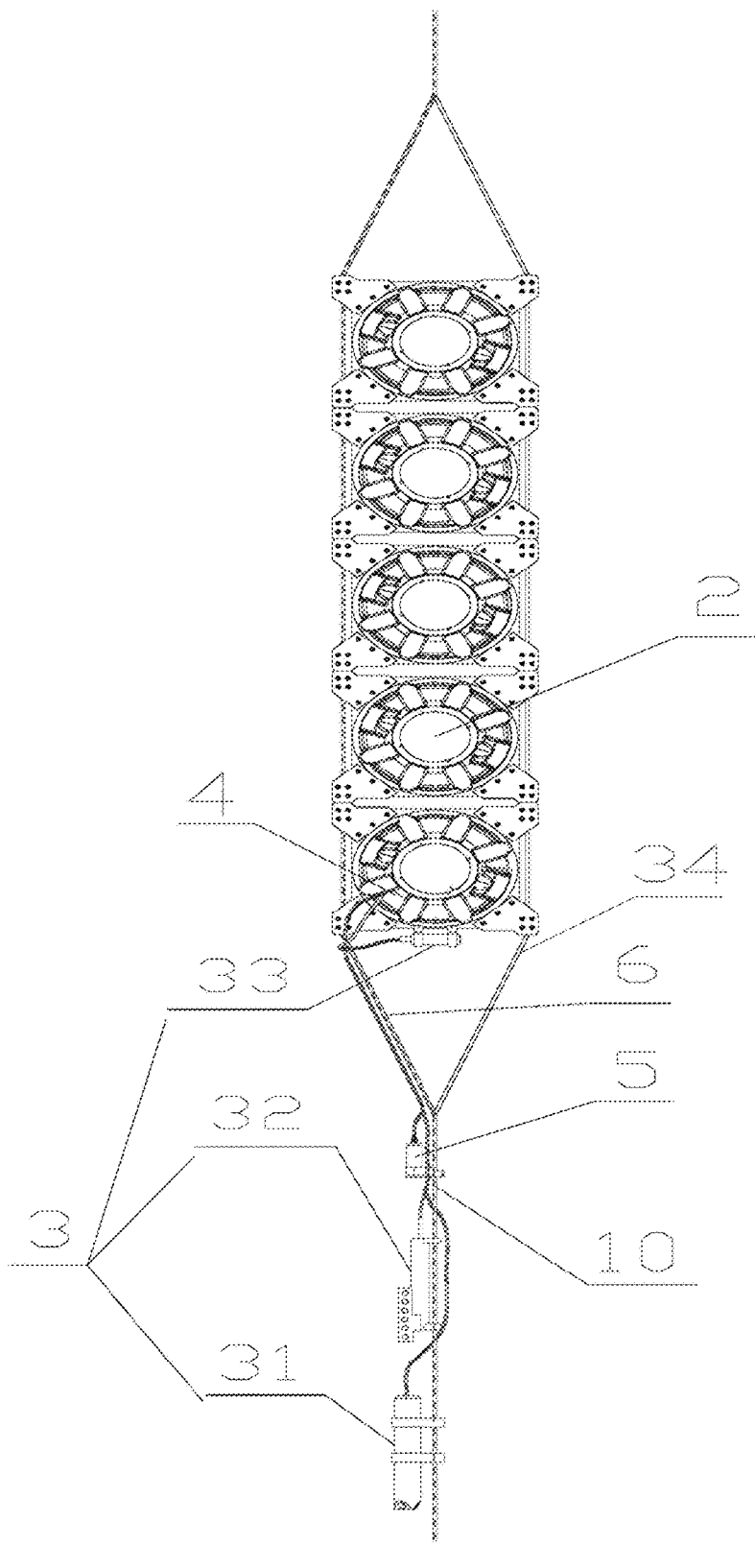
FIG. 2 is a schematic structural diagram of a methane monitoring apparatus according to the present invention.
Figure 3:
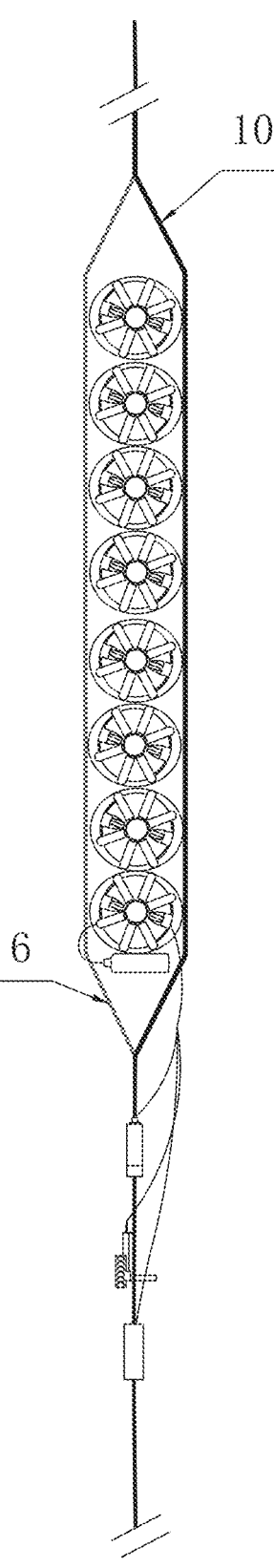
FIG. 3 is a schematic structural diagram of a methane monitoring apparatus according to the present invention.

As shown in FIG. 1 and FIG. 2, a system for stereoscopic and real-time monitoring of an ocean methane profile includes a waterborne communication floating body 7, a submarine gravity anchor 8, and a monitoring mechanism disposed between the waterborne communication floating body 7 and the gravity anchor 8. The monitoring mechanism includes a submarine methane leakage intensity monitoring apparatus 12, a plurality of methane monitoring apparatus 1, and a plastic-coated steel cable 10 connected between the waterborne communication floating body 7 and the gravity anchor 8. The submarine methane leakage intensity monitoring apparatus 12 includes a second communication module and an acoustic Doppler current profiler (ADCP) that is disposed between the gravity anchor 8 and the methane monitoring apparatus 1. The ADCP is connected to the plastic-coated steel cable 10 through the second communication module. A data acquisition cabin 4 of the methane monitoring apparatus is connected with the plastic-coated steel cable 10 through a first communication module 5. A first floating ball assembly 2 of the methane monitoring apparatus is connected to the plastic-coated steel cable 10 through a fixing rope 6. In this embodiment, the plastic-coated steel cable 10 connects the methane monitoring apparatus 1 at different depths together. In addition, the plastic-coated steel cable 10 is further used as a communication cable, and is configured to communicate between the methane monitoring apparatus 1 and the waterborne communication floating body 7, thereby replacing a conventional communication cable and simplifying the monitoring system.

Specifically, the methane monitoring apparatus 1 includes a plurality of first floating ball assemblies 2 for submerging, a real-time monitoring module 3 for synchronous monitoring of methane content and a hydrodynamic environment in a water body, a data acquisition cabin 4 for processing monitored data, a first communication module 5 connected with an external communication apparatus, and a fixing rope 6 for connecting the first floating ball assemblies 2 and the data acquisition cabin 4. The real-time monitoring module 3 is connected with the first communication module 5 through the data acquisition cabin 4. The first floating ball assemblies 2 are connected to the data acquisition cabin 4 through the fixing rope 6. Preferably, the system further includes an upper connector and a lower connector. One end of the fixing rope 6 is connected to a side, close to the waterborne communication floating body 7, of the plastic-coated steel cable 10 through the upper connector; the other end of the fixing rope 6 is connected to a side, close to the gravity anchor 8, of the plastic-coated steel cable 10 through the lower connector, and the data acquisition cabin 4 and the first floating ball assembly 2 are sequentially arranged on the fixing rope 6 in a monitoring direction. In this embodiment, the upper connector and the lower connector may be buckles, U-shaped chucks, or the like made of stainless steel or another material having a high corrosion resistance and compression resistance. Two ends of the fixing rope are connected to the plastic-coated steel cable 10 through the upper connector and the lower connector respectively, so that the first floating ball assemblies 2 are uniformly and sequentially arranged in the monitoring direction under the traction of the fixing rope. Preferably, the data acquisition cabin 4 is also connected to the fixing rope. The fixing rope 6 replaces the plastic-coated steel cable 10 in bearing stress to reduce a breakage risk of the plastic-coated steel cable 10, thereby further solving the problem that it is difficult to assemble a heavy-weight measuring instrument on the plastic-coated steel cable 10. Preferably, the data acquisition cabin 4 is connected to a side, close to the real-time monitoring module 3, of the first floating ball assembly 2 to shorten a communication line. In addition, shapes of the data acquisition cabin 4 and the first floating ball assembly 2 are substantially the same, so that stress on the data acquisition cabin 4 is consistent with stress on the first floating ball assembly 2. This reduces risks of cable breakage and loss between the data acquisition cabin 4 and the first floating ball assembly 2.

Preferably, the real-time monitoring module 3 includes an ocean current meter 31, a CTD 32, and a methane sensor 33; and the ocean current meter 31, the CTD 32, and the methane sensor 33 are all connected to the data acquisition cabin 4, so that methane content and hydrodynamic data such as temperature, salinity, and ocean current of a target water area are acquired, and stored in the data acquisition cabin 4 for processing. Then, the first communication module 5 sends the data to the outside, thereby determining a diffusion path and a destination of methane leaking form the seabed under the control of a hydrodynamic environment. Preferably, the first communication module 5 includes an inductive coupling transmitter for communicating with the outside, and the data acquisition cabin is connected to the external communication apparatus through the inductive coupling transmitter. Preferably, the external communication apparatus includes but is not limited to the waterborne communication floating body 7, an external working vessel, or a satellite. In this embodiment, the data acquisition cabin 4 sends data acquired by the real-time monitoring module 3 to the inductive coupling transmitter in the form of an electrical signal. Then, the inductive coupling transmitter converts the acquired electrical signal to a magnetic signal, and transmits the magnetic signal to the plastic-coated steel cable 10. Subsequently, the waterborne communication floating body 7 acquires the magnetic signal on the plastic-coated steel cable 10, converts the magnetic signal to an electrical signal, and sends the electrical signal to the external working vessel or satellite. Therefore, monitored data in the real-time monitoring module 3 can be sent to an external data collection department in real time, and a worker can learn a vertical gradient of methane and hydrodynamic variation in the target water area in real time, thereby deducing an impact of methane leaking from the seabed on a plurality of water layers and a diffusion and migration path of the methane in a water body. This punctually provides environmental impact assessment and a coping strategy for hydrate exploitation projects. Further, in this embodiment, according to a monitoring need, the waterborne communication floating body 7 and the monitoring mechanism may also send the monitored data regularly, thereby prolonging time of endurance.

Preferably, the submarine methane leakage intensity monitoring apparatus 12 is disposed between the acoustic release 9 and the methane monitoring apparatus 1. The submarine methane leakage intensity monitoring apparatus 12 includes a second communication module and an ADCP that is configured to measure an echo intensity of a water body close to the seabed and an eruption speed of submarine methane. Preferably, the second communication module is also an inductive coupling transmitter for communicating with the outside, that is, data acquired by the ADCP is also sent to the inductive coupling transmitter in the form of an electrical signal, and then transmitted to the waterborne communication floating body 7 by the inductive coupling transmitter through the plastic-coated steel cable 10. In this embodiment, the ADCP with an acoustic frequency of 75 KHz may be used to further monitor leakage and eruption intensities of methane within 400 meters from the seabed, thereby providing an initial field for analyzing diffusion and migration of methane in a middle layer and an upper layer of an ocean. Preferably, the acoustic release 9 is also provided between the plastic-coated steel cable 10 and the gravity anchor 8. Specifically, the lower end of the acoustic release 9 is connected to the gravity anchor 8 through a stainless steel anchor chain, and the upper end of the acoustic release 9 is connected to the monitoring mechanism through the plastic-coated steel cable 10. When a monitoring operation is completed, a mechanical decoupling machine in the acoustic release 9 is controlled to work. The mechanical decoupling machine of the acoustic release 9 is separated from the stainless steel anchor chain, so that the acoustic release 9 is separated from the gravity anchor 8. Therefore, the whole system floats to the sea surface under the action of buoyancy provided by the floating ball assembles, thereby facilitating recycling. Preferably, the system further includes a plurality of second floating ball assemblies 11; and a side, away from the gravity anchor 8, of the acoustic release 9 is connected to the second floating ball assemblies 11. After the mechanical decoupling machine in the acoustic release 9 completes the decoupling operation, the second floating ball assemblies 11 provide upward buoyancy for the acoustic release 9, so that the acoustic release 9 can be separated from the gravity anchor 8 as soon as possible. Therefore, a probability of success separation is improved.

In this embodiment, the gravity anchor 8 sinks down to the seabed; and the methane monitoring apparatus 1 and the submarine methane leakage intensity monitoring apparatus 12 that are connected to the plastic-coated steel cable 10 are fixed in the target water area through the plastic-coated steel cable 10. Preferably, the plurality of methane monitoring apparatus 1 and the submarine methane leakage intensity monitoring apparatus 12 on the plastic-coated steel cable 10 are arranged from the waterborne communication floating body 7 to the gravity anchor 8 to monitor synchronously a methane concentration and a hydrodynamic environment of a target sea area by water layers and stereoscopically track a diffusion and migration path, in a water body, of methane leaking from a seabed. Specifically, the submarine methane leakage intensity monitoring apparatus 12 uses the ADCP to monitor an echo intensity of the water body and an eruption speed of submarine methane, thereby determining a leakage intensity of submarine methane. The ocean current meter 31, the CTD 32, and the methane sensor 33 in the real-time monitoring module 3 of each methane monitoring apparatus 1 respectively acquire an ocean current, temperature, salinity, and methane content of a corresponding water layer, and then store the data in the data acquisition cabin 4 respectively. The data acquisition cabin 4 sends the data acquired by the real-time monitoring module 3 to the inductive coupling transmitter in the form of an electrical signal. Then, the inductive coupling transmitter converts the acquired electrical signal to a magnetic signal, and transmits the magnetic signal to the plastic-coated steel cable 10. Subsequently, the waterborne communication floating body 7 acquires the magnetic signal on the plastic-coated steel cable

10, converts the magnetic signal to an electrical signal, and sends the electrical signal to the external working vessel or satellite.

For those skilled in the art, various other corresponding changes and modifications can be made based on the technical solutions and concepts described above, and all these changes and modifications should fall within the protection scope of the claims of the present invention.

What is claimed is:

1. A methane monitoring apparatus, comprising:
a plurality of first floating ball assemblies for submerging, wherein each first floating ball assembly comprises at least two floating ball that are vertically stacked and coupled to a fixing rope,
a real-time monitoring module comprising an ocean current meter, a Conductivity Temperature Depth (CTD), and a methane sensor, each of which is hard-wired to a common data acquisition cabin for simultaneous time-stamped acquisition of ocean current, temperature, salinity, and methane content,
a data acquisition cabin for processing monitored data,
a first communication module connected with an external communication apparatus, and
a fixing rope for connecting the plurality of first floating ball assemblies and the data acquisition cabin, wherein the real-time monitoring module is connected with the first communication module through the data acquisition cabin, and the plurality of first floating ball assemblies are connected to the data acquisition cabin through the fixing rope, wherein the first communication module communicates with outside of the methane monitoring apparatus, and the fixing rope does not communicate with the outside of the methane monitoring apparatus.

2. The methane monitoring apparatus according to claim 1, wherein the plurality of first floating ball assemblies are sequentially arranged on the fixing rope in a monitoring direction.

3. The methane monitoring apparatus according to claim 1, wherein the fixing rope is a Kevlar rope.

4. The methane monitoring apparatus according to claim 1, wherein the first communication module comprises an inductive coupling transmitter for communicating with the outside, and the data acquisition cabin is connected to the external communication apparatus through the inductive coupling transmitter.

5. The methane monitoring apparatus according to claim 1, wherein each of the plurality of first floating ball assemblies comprises a glass floating ball and a protective shell wrapping the glass floating ball, and the glass floating ball is connected to the fixing rope through the protective shell.

6. A system for stereoscopic and real-time monitoring of an ocean methane profile, comprising a waterborne communication floating body, a submarine gravity anchor, and a monitoring mechanism disposed between the waterborne communication floating body and the gravity anchor, wherein
the monitoring mechanism comprises a first methane monitoring apparatus, a second methane monitoring apparatus and a plastic-coated steel cable connected between the waterborne communication floating body and the gravity anchor, wherein the first methane monitoring apparatus is a submarine methane leakage intensity monitoring apparatus, and the second methane monitoring apparatus is the methane monitoring apparatus according to claim 1;

the submarine methane leakage intensity monitoring apparatus comprises a second communication module and an acoustic Doppler current profiler (ADCP), wherein the ADCP is disposed between the gravity anchor and the methane monitoring apparatus; the ADCP is connected to the plastic-coated steel cable through the second communication module; the data acquisition cabin of the methane monitoring apparatus is connected with the plastic-coated steel cable through the first communication module; the plurality of first floating ball assemblies of the methane monitoring apparatus is connected to the plastic-coated steel cable through the fixing rope; and the plastic-coated steel cable is configured to communicate between the methane monitoring apparatus and the waterborne communication floating body.

7. The system according to claim 6, further comprising an upper connector and a lower connector, wherein a first end of the fixing rope is connected to a first side, close to the waterborne communication floating body, of the plastic-coated steel cable through the upper connector; a second end of the fixing rope is connected to a second side, close to the gravity anchor, of the plastic-coated steel cable through the lower connector.

8. The system according to claim 6, further comprising an acoustic release, wherein the plastic-coated steel cable is connected to the gravity anchor through the acoustic release; and the ADCP is disposed between the acoustic release and the methane monitoring apparatus.

9. The system according to claim 8, further comprising a plurality of second floating ball assemblies wherein a side, away from the gravity anchor, of the acoustic release is connected to the plurality of second floating ball assemblies through the fixing rope.

10. The system according to claim 6, wherein, in the methane monitoring apparatus, the fixing rope is a Kevlar rope.

11. The system according to claim 6, wherein, in the methane monitoring apparatus, the first communication module comprises an inductive coupling transmitter for communicating with the outside, and the data acquisition cabin is connected to the external communication apparatus through the inductive coupling transmitter.

12. The system according to claim 6, wherein, in the methane monitoring apparatus, each of the plurality of first floating ball assemblies comprises a glass floating ball and a protective shell wrapping the glass floating ball, and the glass floating ball is connected to the fixing rope through the protective shell.

* * * * *